(12) United States Patent
Voitsechov

(10) Patent No.: US 10,531,920 B1
(45) Date of Patent: Jan. 14, 2020

(54) METHOD AND DEVICE FOR SKIN TREATMENT USING LASER DIODE BARS EMITTING DIFFERENT LASER WAVELENGTHS

(71) Applicant: Invasix Ltd., Richmond Hill (CA)

(72) Inventor: Uri Voitsechov, Moshav Amirim (IL)

(73) Assignee: INVASIX LTD., Richmond Hill, Ontario (CA)

( * ) Notice: Subject to any disclaimer, the term of this patent is extended or adjusted under 35 U.S.C. 154(b) by 918 days.

(21) Appl. No.: 15/090,085

(22) Filed: Apr. 4, 2016

(51) Int. Cl.
| | |
|---|---|
| *A61B 18/18* | (2006.01) |
| *A61B 18/20* | (2006.01) |
| *A61N 5/06* | (2006.01) |
| *A61B 18/00* | (2006.01) |
| *A61B 18/22* | (2006.01) |
| *A61N 5/067* | (2006.01) |

(52) U.S. Cl.
CPC .......... *A61B 18/203* (2013.01); *A61N 5/0616* (2013.01); *A61B 2018/0016* (2013.01); *A61B 2018/00452* (2013.01); *A61B 2018/00476* (2013.01); *A61B 2018/207* (2013.01); *A61B 2018/225* (2013.01); *A61N 2005/067* (2013.01); *A61N 2005/0644* (2013.01); *A61N 2005/0659* (2013.01); *A61N 2005/0662* (2013.01)

(58) Field of Classification Search
CPC .......... A61B 18/203; A61B 2018/0016; A61B 2018/00452; A61B 2018/00476; A61B 2018/207; A61B 2018/225; A61N 5/0616; A61N 2005/0644; A61N 2005/0659; A61N 2005/0662; A61N 2005/067
USPC .......................................................... 606/9
See application file for complete search history.

(56) References Cited

U.S. PATENT DOCUMENTS

| | | |
|---|---|---|
| 5,595,568 A | 1/1997 | Anderson et al. |
| 2009/0254068 A1 | 10/2009 | Karni et al. |
| 2012/0165800 A1 | 6/2012 | Keeney et al. |
| 2013/0066237 A1* | 3/2013 | Smotrich ............... A61N 5/022 601/2 |

* cited by examiner

Primary Examiner — Aaron F Roane
(74) Attorney, Agent, or Firm — Allen Dyer Doppelt & Gilchrist

(57) ABSTRACT

A method and device for skin treatment include using a laser diode bar stack to generate a mix of at least two laser wavelengths for application to a skin area to be treated.

17 Claims, 4 Drawing Sheets

METHOD AND DEVICE FOR SKIN TREATMENT USING LASER DIODE BARS EMITTING DIFFERENT LASER WAVELENGTHS

FIELD OF THE INVENTION

The invention relates to skin treatment using lasers, and more particularly to methods and devices for skin treatment incorporating laser diodes.

BACKGROUND OF THE INVENTION

Laser-based dermatological treatment gained high popularity in aesthetic medicine and laser hair removal is the most popular medical cosmetic application. U.S. Pat. No. 5,595,568 describes a method of permanent hair removal using lasers of different wavelengths, the contents of which patent are herein incorporated by reference in their entirety. This method of hair removal is based on principles of selective photothermolisis, including the following:
  a. Light should penetrate into the skin deep enough to reach treated target; and
  b. Light absorption in the target should be higher than in surrounding tissue.

The most suitable wavelengths for hair removal are in the range of 600 nm to 1100 nm, with longer wavelengths in the range being safer for darker skin and shorter wavelengths being more effective for hair follicle destruction, but less safe for darker skin. Wavelengths longer than 1200 nm are generally not used for hair removal because of absorption by water. These longer wavelengths can be used for unselective heating of skin and fat. Wavelengths shorter than 600 nm have achieve minimal penetration depth, on the order of 1.5 mm or less, and are therefore not effective for hair removal.

The most popular lasers used for hair removal are:
  a. Ruby lasers with a wavelength of 694 nm. Lasers with this wavelength have very high absorption in melanin, which is the main chromophor in the hair and the epidermis, but the penetration depth of this wavelength is not very high. These lasers are considered to be very hard on the epidermis, and their use has declined significantly in recent years.
  b. Alexandrite lasers with a wavelength of 755 nm are very effective for hair removal, but less safe for darker skin.
  c. Laser diodes with wavelengths of 800 nm-820 nm, which are considered safe and effective for most of the skin types, but can be less effective for removal of fine and lighter hairs.
  d. Nd:YAG (neodymium-doped yttrium aluminum garnet) lasers with a wavelength of 1064 nm. This laser has an excellent penetration depth, but not very high absorption in the melanin. As a result it is very safe for all skin types, but effective for removal of black and coarse hairs only.

There are no optimal wavelengths between 820 nm and 1064 nm because of a broad peak of water absorption which limits light penetration depth.

Recently, laser diode technology has developed dramatically and effective lasers with a wide range of different wavelengths are now available. U.S. Patent Application Publication No. 2009/0254068 describes a device and method of hair removal using a laser diode laser with a wavelength 750 nm to 1500 nm, applied in pulses with a high repetition rate, the contents of which application are herein incorporated by reference in their entirety. Laser diodes are also used for treatment of vascular lesions, collagen remodeling, fat destruction and other therapeutic applications and treatments.

Wavelengths of laser diodes can be selected during the design of treatment devices, but a single laser wavelength does not always provide optimal treatment and combination of two or more laser wavelengths can be preferable. For example, U.S. Patent Application Publication No. 2012/0165800 describes a device with a few single laser diode emitters, which emitters may have different wavelengths. However, single laser diodes emitters are not powerful enough for the majority medical and cosmetic applications where selective coagulation of tissue is required.

SUMMARY OF THE INVENTION

In view of the foregoing, the present invention provides methods and devices to generate significant power from stacks of laser diode bars, while simultaneously generating multiple laser wavelengths. For example, the invention includes a method and device for applying optical energy to the skin surface using stack of laser diode bars, where alternating diode bars in the stack to generate a mix of two or more laser wavelengths irradiating the same skin surface.

In one embodiment, a hand piece of the device includes a stack of at least two laser diode bars configured to emit two different laser wavelengths. Advantageously, one laser wavelength is shorter than 790 nm and the other laser wavelength is longer than 790 nm. More preferably, one laser wavelength is in the range of 700 nm to 790 nm and the other wavelength is 790 nm to 1200 nm.

In an embodiment of the device for dark skin treatment, the hand piece includes a stack of at least two laser diode bars configured to emit at least two different laser wavelengths, wherein both wavelengths are longer than 790 nm. Advantageously, longer wavelengths can be used in applications where deeper penetration of light is required.

In another embodiment of the device for fine and lighter hair treatment, the hand piece includes stack of at least two laser diode bars, where the laser diode bars are configured to emit different laser wavelengths that are both shorter than 790 nm.

In another embodiment for vascular lesion treatment, the hand piece comprises stack of a stack of at least two laser diode bars, where the laser diode bars are configured to emit different laser wavelengths that are both longer than 840 nm but shorter than 1200 nm.

In another embodiment for treatment of skin including subcutaneous fat, the hand piece comprises a stack of at least two laser diode bars, where the laser diode bars are configured to emit different laser wavelengths that are both longer than 840 nm but shorter than 1300 nm.

In some embodiments, groups of laser diode bars configured to emit the same laser wavelength alternate with other laser diode bars (or groups thereof) configured to emit a different laser wavelength. For example, a group of two laser diode bars, both configured to emit a laser wavelength of 808 nm can be arranged adjacent to a single laser diode bar configured to emit a laser wavelength of 755 nm. Numbers of laser diode bars and wavelengths in each group can varied depending on desired device design objectives and applications.

A stack of laser diode bars configured to emit more than two laser wavelengths can be employed allowing for fine tuning of treatment parameters for multiple specific applications using the same hand piece.

The light generated by laser diode bar stack is delivered via a delivery mechanism such as a light guide and/or output window and then to a patient's skin. The light guide can be rigid or flexible. Preferably, the light guide is in contact with the patient's skin during administration of a treatment, but some embodiments can be located at some distance from the skin during treatment.

In general, the distance between the laser diode bar stack and the skin to be treated is preferably short enough to avoid strong light beam divergence and reduction of energy density below a level needed for the treatment. On the other side, the distance is preferably long enough to allow mixing of different laser wavelengths to produce an essentially uniform distribution of the different laser wavelengths on the skin surface.

This mixing of different wavelength can be accomplished in the light guide due to natural divergence of generated rays of light. Alternatively, or in combination with the light guide, diffusers or other optical elements can be used to optimize light uniformity as delivered to the skin surface.

The laser diode bar stack is preferably cooled by liquid coolant liquid circulated therethrough. The liquid coolant can be close to room temperature or pre-cooled. Liquid coolant temperature can increase during laser operation.

The light guide can also be cooled to protect the epidermis from overheating during treatment. The light guide can be cooled directly by thermo-electric coolers or by the circulation of pre-cooled coolant. As noted, the length of light guide should be long enough that the laser light generated by different laser diode bars is mixed and uniform in fluence with a homogeneous mix of wavelengths applied to the treated skin surface.

The light generated by the laser diode bar stack is applied to the skin in a pulsed manner with a pulse duration varying from 1 ms to 300 ms. The laser pulse can be generated as a single pulse or as a train of pulses but an overall duration of energy application to the treated skin preferably does not exceed 400 ms. Longer pulses generally lower effectiveness because of strong heat dissipation from the hair follicle. After applying the pulse of energy, the hand piece is moved to the next spot to treat another skin area (e.g., the next area of hairs to be treated). Multiple passes of pulses can be applied to the same area to ensure uniform coverage and effective treatment. For some applications, continuous application of laser energy can be used.

The electrical connection of the laser diode bars within a stack is preferably serial; therefore when a applying a pulse of electrical power to the laser diode bar stack, all the bars generate laser light substantially simultaneously, regardless of wavelength. Thus, the mix of two or more laser wavelengths is provided with each pulse. A preferred average pulse power generated by single laser bar is in the range of 10 W to 200 W. In addition, average fluence delivered to the patient for hair removal is varied from 5 $J/cm^2$ up to 100 $J/cm^2$. Light fluence can go higher for longer wavelengths to treat stubborn hairs. A complete treatment device advantageously includes the following elements:

1. One or more user interfaces with LCD or other indicator allowing easy visualization of treatment settings and device status, along with a touch screen, keypad or other input device allowing a user to set treatment parameters.
2. Support equipment including a liquid coolant circulating system configured to supply cooling to the laser diode bar stack and/or light guide, and an electrical power supply configured to generate the pulses of electrical power transmitted to the laser diode bar stack.
3. A hand piece including the laser diode bar stack, with connections to supply cooling and electrical power thereto from the support equipment. The hand piece advantageously also includes the light guide and independent cooling elements for the light guide and skin cooling.

A light spectrum width generated by each laser diode bar in the stack will vary based on quality and operating parameters of the bar. Generally, the spectrum width may be up to 30 nm, can also shift slightly depending on operating temperature.

In a preferred embodiment for light skin hair removal, the laser diode bar stack includes from 8 to 20 bars with alternate bars emitting laser wavelengths of 755 nm+/−15 nm and 810 nm+/−15 nm, respectively.

In a preferred embodiment for dark skin hair removal, the laser diode bar stack includes from 8 to 20 bars with alternate bars emitting laser wavelengths of 810 nm+/−15 nm and 1060 nm+/−10 nm, respectively.

According to a method aspect, a treatment method includes steps of:

1. Setting treatment parameters via the user interface.
2. Placing the hand piece output window at least proximate the skin surface in a first area to be treated.
3. Initiating treatment by applying the electrical pulse(s) to the laser diode bar stack to generate pulse(s) of optical energy with a mix of two or more laser wavelengths.
4. Moving the hand piece to each additional area of the ricin surface to be treated and repeating 3, above.
5. Performing additional passes of the areas to be treated, repeating 3, above, as necessary for complete and uniform treatment.
6. Skin cooling can also be performed before, during and/or after the application of optical energy to the skin surface to reduce skin temperature.

The device can be applied to broad range of dermatological applications requiring thermolysis of different targets on and/or below the skin surface. Not limiting examples of such applications include: permanent and temporary hair growth reduction; treatment of vascular and pigmented lesions; acne treatment; collagen remodeling for skin tightening; wrinkle and cellulite reduction; and hyperhidrosis.

These and other objects, aspects and advantages of the present invention will be better appreciated in view of the drawings and following detailed description of preferred embodiments.

DETAILED DESCRIPTION OF PREFERRED EMBODIMENTS

Figure 1:
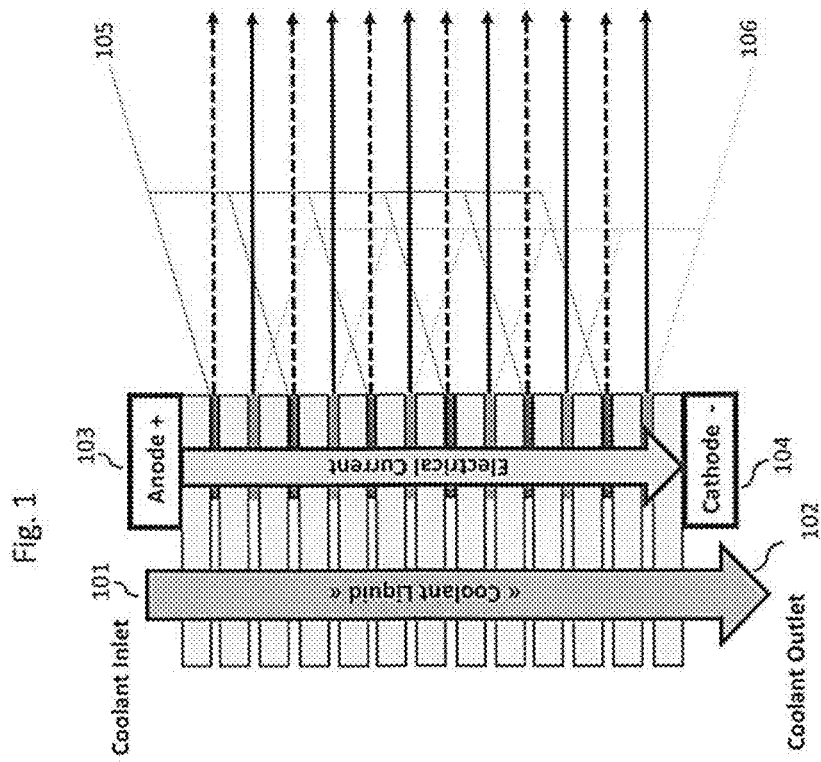
FIG. 1 is a schematic view of a laser diode bar stack where laser wavelengths emitted alternate between each adjacent laser diode bar.

Referring first to FIG. 1, a laser diode bar stack is shown, a first laser wavelength emitted therefrom being represented by dashed arrows and a second laser wavelength emitted therefrom being represented by solid arrows. Coolant flow (e.g., water) enters the laser diode bar stack through a coolant inlet 101 to cool the laser diode bars and then exits through a coolant outlet 102. Pulses of electrical power are applied to the laser diode bar stack through the contacts 103 (anode) and 104 (cathode). The first laser diode bars 105 are configured to emit the first laser wavelength and the second laser diode bars 106 are configured to emit the second laser wavelength.

Figure 2:
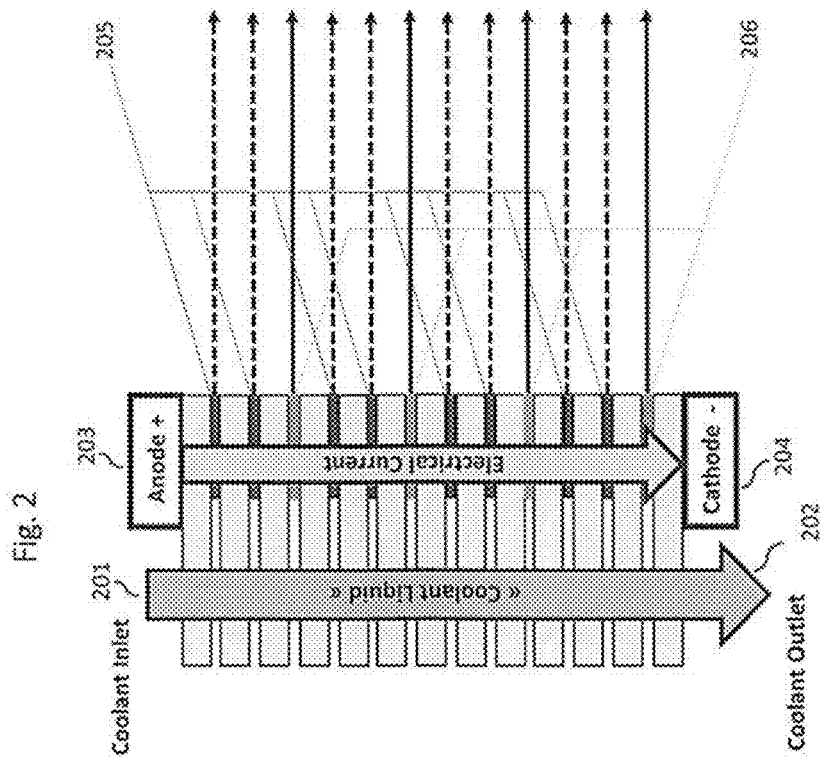
FIG. 2 is a schematic view of a laser diode bar stack where two laser diode bars emitting a first laser wavelength alternate with individual laser diode bars emitting a second laser wavelength.

Referring to FIG. 2, an alternate laser diode bar stack is shown. With dashed and solid arrows representing first and second laser wavelengths emitted therefrom, as in FIG. 1. Also as in FIG. 1, coolant flow enters the laser diode bar stack through a coolant inlet 201, cools the laser diode bars, and exits via a coolant outlet 202, and pulses of electrical power are applied through the contacts 203 (anode) and 204 (cathode). First laser diode bars 205 are configured to emit the first laser wavelength and second laser diode bars 206 are configured to emit the second laser wavelength. As will be appreciated, a single second laser diode bar 206 is placed adjacent each group of two first laser diode bars 205.

Figure 3:
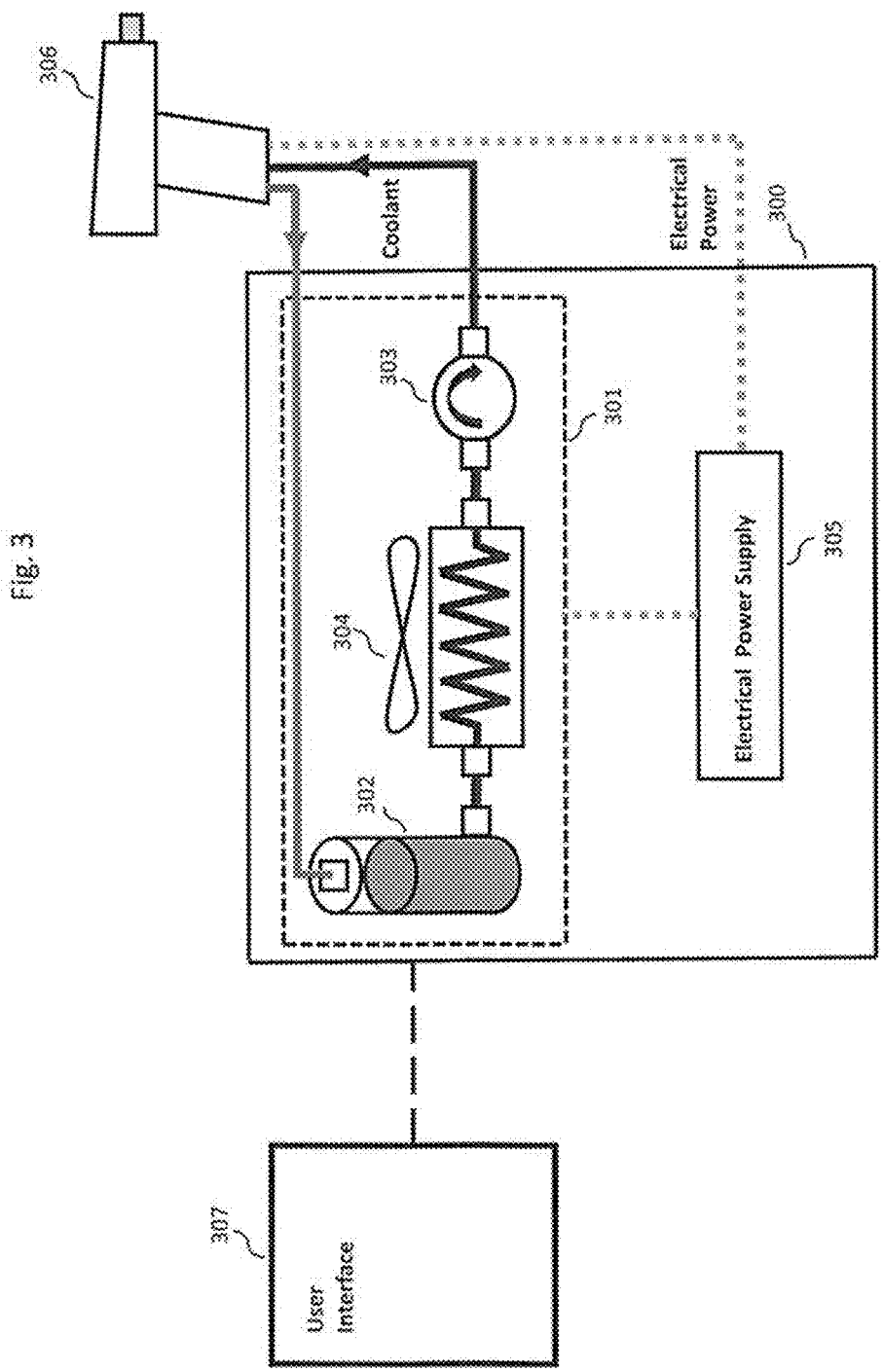
FIG. 3 is a schematic block diagram of a device for hair removal, including a handpiece and support equipment.

Referring to FIG. 3, the laser treatment device includes support equipment 300, which can advantageously be located on a common platform. The support equipment 300 includes a cooling system 301 and an electrical power supply 305. The cooling system 301 includes coolant reservoir 302, a coolant pump 303 for circulating the coolant through the hand piece 306, and a heat exchanger 304 for removing heat from the warmer coolant returning from the hand piece 306.

The power supply 305 generates the pulses of electrical power required by the hand piece 306 to generate the pulses of optical (laser) energy, per whatever treatment parameters are selected via the user interface 307. The user interface 307 and/or support equipment incorporate one or more processors and non-transient memory storage devices to receive treatment parameter settings from users, calculate operational settings based thereon, control the supply of electrical power and/or cooling, and display device and treatment status information to users.

Figure 4:
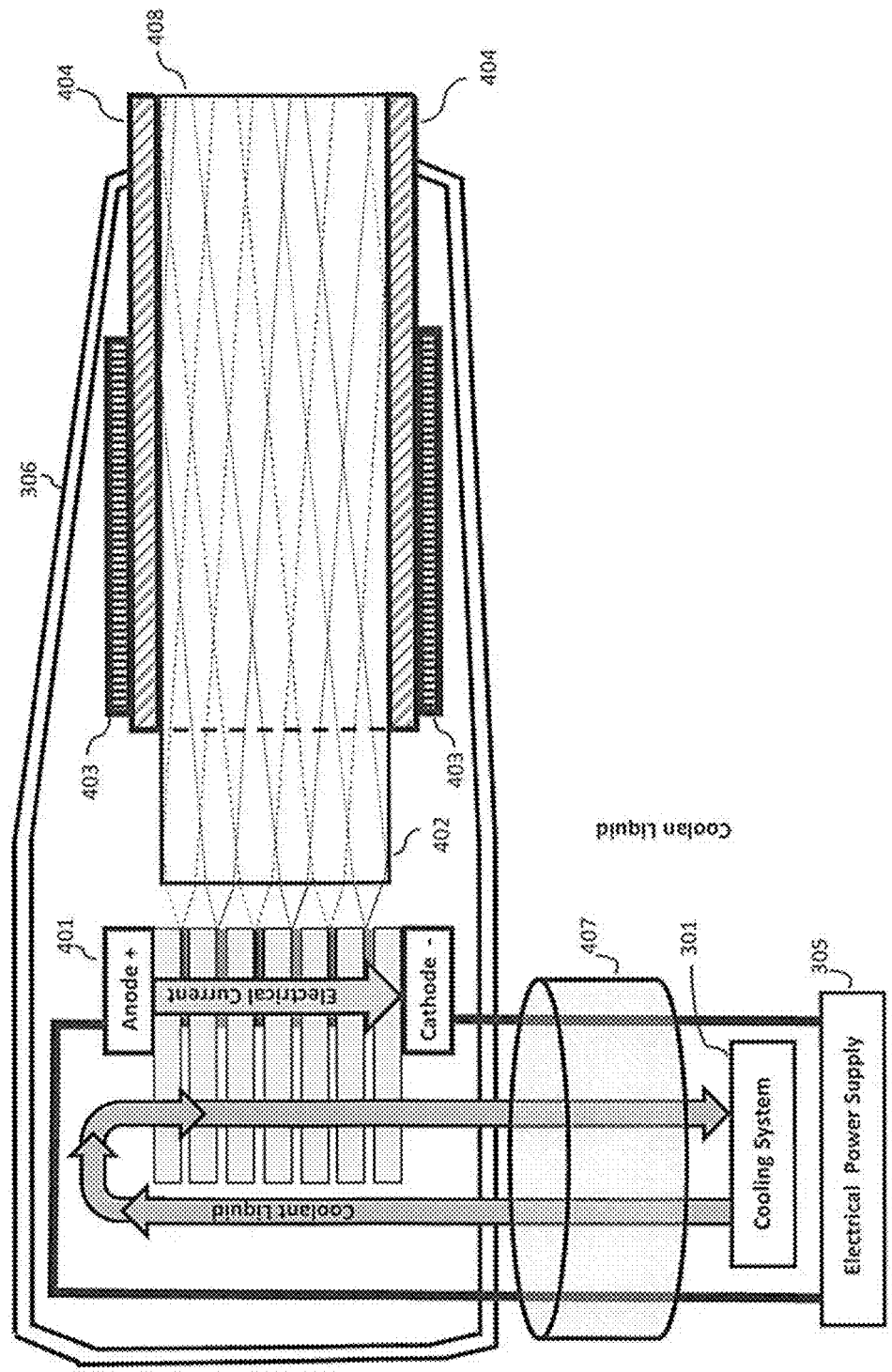
FIG. 4 is schematic view of the handpiece of FIG. 3.

Referring to FIG. 4, the laser diode stack 401 is located in the hand piece 306. A transparent light guide 402 is located in the hand piece 306 in the path of laser light emitted from the stack 401, thereby collecting the optical radiation and delivering it to the skin surface. Thermo-electric cooling elements 403 are attached to a metal sleeve 404 surrounding the light guide 402. The metal sleeve 404 around the light guide 402 allows more effective cooling of light guide and the skin surface placed in contact therewith, enhancing treatment safety. The optical energy (in the form of a plurality of different wavelengths) generated by the laser diode bar stack 401 passes through the light guide 402 and out the output window 408 prior to delivery to the skin surface to be treated. A harness 407 includes electrical wires and coolant tubes for connection with the cooling system 301 and electrical power supply 305 of the support equipment 300 (see also, FIG. 3).

According to a method of treatment:
1. treatment parameter are set including treatment fluence, pulse duration and pulse structure via the user interface;
2. the device calculates the parameters of the electrical power to be supplied, including the electrical current, pulse width and structure, based on the set treatment parameters:
3. the hand piece output window is placed adjacent to the skin area to be treated; and
4. the electrical pulses are generated by the power supply and delivered to the hand piece to generate the multiple laser wavelengths for delivery to the skin area to be treated.

The foregoing description is provided for illustrative and exemplary purposes; the present invention is not necessarily limited thereto. Rather, those skilled in the art will appreciate that various modifications, as well as adaptations to particular circumstances, are possible within the scope of the invention as herein shown and described.

What is claimed is:

1. A device for skin treatment comprising:
a hand piece having a laser diode bar stack, the laser diode bar stack including at least one first laser diode bar configured to emit a first laser wavelength and at least one second laser diode bar configured to emit a second laser wavelength, the first and second laser wavelengths being different, and a delivery mechanism configured to convey the first and second laser wavelengths to a skin area to be treated;
wherein the laser diode bar stack includes respective pluralities of the first and second laser diode bars; and
wherein multiple bars of the plurality of first laser diode bars alternate with at least one bar of the plurality of second laser diode bars.

2. The device of claim 1, wherein the delivery mechanism is configured to deliver a substantially uniform distribution of the first and second laser wavelengths to the skin area to be treated.

3. The device of claim 2, wherein the delivery mechanism includes a light guide having a first end located adjacent to the laser diode bar stack and a second end configured for placement proximate the skin area to be treated.

4. The device of claim 3, wherein a length of the light guide is dimensioned to allowing mixing of the first and second laser wavelengths to achieve the substantial uniform distribution of the first and second laser wavelengths to the skin area to be treated.

5. The device of claim 3, wherein an output window is arranged at the second end of the light guide.

6. The device of claim 1, wherein the first laser wavelength is shorter than 790 nm and the second laser wavelength is longer than 790 nm.

7. The device of claim 1, wherein the first and second laser wavelengths are both longer than 790 nm.

8. The device of claim 1, wherein the first and second laser wavelengths are both shorter than 790 nm.

9. The device of claim 1, wherein the first and second laser wavelengths are both in the range of 600 nm to 1100 nm.

10. The device of claim 1, further comprising an electrical power supply configured to supply electrical power to the laser diode bar stack of the hand piece.

11. The device of claim 10, wherein the electrical power supply is configured to supply pulses of electrical power having a duration in the range of 5 ms to 300 ms.

12. The device of claim 10, wherein the electrical power supply is configured to supply electrical power to the laser diode stack to achieve an applied output of laser energy to the skin area to be treated in the range of 3 $J/cm^2$ to 100 $J/cm^2$.

13. The device of claim 1, wherein the handpiece further includes a cooling system configured to cool the skin area to be treated when placed adjacent thereto.

14. A method of using the device of claim 1, the method comprising:
placing the hand piece proximate the skin area to be treated; and powering the laser bar stack to apply a mix of the first and second laser wavelengths to the skin area to be treated via the delivery mechanism.

15. The method of claim 14, wherein the method is performed for hair removal from the skin area to be treated.

16. The method of claim 14, wherein the method further comprises cooling the skin area to be treated during at least one of: a period prior to application of the mix of first and second laser wavelengths; a period during application of the mix of first and second laser wavelengths; and a period after application of the mix of first and second laser wavelengths.

17. The method of claim 14, wherein the method further comprises cooling the skin area to be treated during all of: a period prior to application of the mix of first and second laser wavelengths; a period during application of the mix of first and second laser wavelengths; and a period after application of the mix of first and second laser wavelengths.

* * * * *